US012546174B2

(12) United States Patent
Stewart et al.

(10) Patent No.: US 12,546,174 B2
(45) Date of Patent: Feb. 10, 2026

(54) AUTOMATED DRILLING FLUIDS MANAGEMENT SYSTEM

(71) Applicant: Schlumberger Technology Corporation, Sugar Land, TX (US)

(72) Inventors: Colin Stewart, Houston, TX (US); Chemsseddine Bouguetta, Houston, TX (US); Adrien Chassard, Houston, TX (US); Bruno Lecerf, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 518 days.

(21) Appl. No.: 18/007,359

(22) PCT Filed: Jul. 30, 2021

(86) PCT No.: PCT/US2021/043859
§ 371 (c)(1),
(2) Date: Jan. 30, 2023

(87) PCT Pub. No.: WO2022/026804
PCT Pub. Date: Feb. 3, 2022

(65) Prior Publication Data

US 2023/0272682 A1 Aug. 31, 2023

Related U.S. Application Data

(60) Provisional application No. 62/706,064, filed on Jul. 30, 2020.

(51) Int. Cl.
*E21B 21/08* (2006.01)
*E21B 21/06* (2006.01)
(Continued)

(52) U.S. Cl.
CPC .............. *E21B 21/08* (2013.01); *E21B 21/06* (2013.01); *E21B 44/00* (2013.01); *E21B 49/08* (2013.01); *G01N 33/2823* (2013.01)

(58) Field of Classification Search
CPC .......... E21B 21/08; E21B 21/00; E21B 49/08; E21B 44/00; E21B 21/06; G01N 33/2823
See application file for complete search history.

(56) References Cited

U.S. PATENT DOCUMENTS

| | | | | |
|---|---|---|---|---|
| 2009/0294174 | A1* | 12/2009 | Harmer | E21B 47/09 175/48 |
| 2012/0272174 | A1 | 10/2012 | Vogel et al. | |

(Continued)

FOREIGN PATENT DOCUMENTS

| | | | |
|---|---|---|---|
| WO | 2012170273 | A1 | 12/2012 |
| WO | 2015174991 | A1 | 11/2015 |
| WO | 2016099489 | A1 | 6/2016 |

OTHER PUBLICATIONS

Substantive Exam issued in Saudi Arabia Patent Application No. 523442380 dated Mar. 14, 2024, 11 pages with English translation.

(Continued)

*Primary Examiner* — Thomas M Hammond, III
(74) *Attorney, Agent, or Firm* — Jeffrey D. Frantz

(57) ABSTRACT

A method for controlling drilling fluid properties includes receiving one or more measurements representing a drilling efficiency of a drilling rig including a drill bit deployed into a well. A drilling rig circulates a drilling fluid in the well. The method includes determining that the one or more measurements are lower than expected, determining that a property of a subterranean formation in which drill bit is positioned has changed based on one or more measurements, and in response to determining that the subterranean formation has changed, automatically generating a drilling
(Continued)

fluid adjustment plan based at least in part on one or more of a drilling fluid inhibition factor or a drilling fluid stability factor.

19 Claims, 8 Drawing Sheets

(51) Int. Cl.

| | |
|---|---|
| ***E21B 44/00*** | (2006.01) |
| ***E21B 49/08*** | (2006.01) |
| ***G01N 33/28*** | (2006.01) |

(56) References Cited

U.S. PATENT DOCUMENTS

| | | | |
|---|---|---|---|
| 2016/0108687 | A1 | 4/2016 | Rapoport |
| 2016/0305231 | A1 | 10/2016 | Majidi et al. |
| 2017/0309614 | A1 | 10/2017 | Kabir |
| 2018/0003654 | A1 | 1/2018 | Chen et al. |
| 2018/0119535 | A1* | 5/2018 | Shen ........................ E21B 45/00 |
| 2018/0223159 | A1 | 8/2018 | Al-Yami |
| 2019/0093468 | A1 | 3/2019 | Aguirre |
| 2020/0165917 | A1 | 5/2020 | Kleinguetl |
| 2020/0347700 | A1* | 11/2020 | Yu ............................ G01V 1/48 |
| 2021/0404271 | A1* | 12/2021 | Ye ...................... G01N 33/2847 |

OTHER PUBLICATIONS

Search and Examination report issued in European Patent Application 21849518.2 on Aug. 7, 2024, 10 pages.

International Preliminary Report on Patentability issued in International Patent application PCT/US2021/043859, mailed Feb. 9, 2023, 8 pages.

Second Substantive Exam issued in Saudi Arabia Patent Application No. 523442380 dated Oct. 16, 2024, 9 pages with English translation.

International Search Report and Written Opinion issued in International Patent Application No. PCT/US2021/043859 dated Nov. 8, 2021, 9 pages.

American Petroleum Institute, "Field Testing Water-based Drilling Fluids", API Recommended Practice 13B-1, 2019, 132 pages.

* cited by examiner

AUTOMATED DRILLING FLUIDS MANAGEMENT SYSTEM

CROSS-REFERENCE TO RELATED APPLICATIONS

This application is a National Stage entry of International Patent Application No. PCT/US2021/043859, filed on Jul. 30, 2021, which claims priority to U.S. Provisional Patent Application No. 62/706,064, filed on Jul. 30, 2020, and is incorporated herein by reference in its entirety.

BACKGROUND

Unless otherwise indicated, this section does not describe prior art to the claims and is not admitted prior art.

Drilling fluids are used in a variety of ways when drilling a well. They can cool and maintain the bits, remove cuttings from a borehole, and/or maintain an appropriate level of pressure within the borehole (for example, heavy enough to prevent the borehole from collapsing or letting gas, oil or fluids enter the borehole but not so heavy that it forces the drilling fluid into the formation). Drilling fluids can have different compositions, yielding different fluid properties, which may be selected to promote performance in a given well under the operating conditions that are present. Given the various roles that drilling fluid can fill, during a typical drilling operation the drilling fluid is being measured, monitored, and adjusted to accommodate the changing conditions as the well progresses.

In current operations, a mud plan is generally created as part of the drilling plan for the well. When the drilling operation is underway, the mud engineers generally make multiple manual measurements and then manually adjust the fluid by making product additions or performing of treatments of the fluid. This process often relies heavily on the specialists' training, experience, and knowhow. However, recently, efforts have been made to reduce rig headcount and expertise of operators through the use of automated decision-making and well plan implementation. This may reduce costs, while provide a more reliable, repeatable drilling operation.

SUMMARY

Embodiments of the disclosure include a method for controlling drilling fluid properties that includes receiving one or more measurements representing a drilling efficiency of a drilling rig including a drill bit deployed into a well. A drilling rig circulates a drilling fluid in the well. The method includes determining that the one or more measurements are lower than expected, determining that a property of a subterranean formation in which drill bit is positioned has changed based on one or more measurements, and in response to determining that the subterranean formation has changed, automatically generating a drilling fluid adjustment plan based at least in part on one or more of a drilling fluid inhibition factor or a drilling fluid stability factor.

Embodiments of the disclosure include a computing system including one or more processors, and a memory system including one or more non-transitory computer-readable media storing instructions that, when executed by at least one of the one or more processors, cause the computing system to perform operations. The operations include receiving one or more measurements representing a drilling efficiency of a drilling rig including a drill bit deployed into a well. A drilling rig circulates a drilling fluid in the well. The operations also include determining that the one or more measurements are lower than expected, determining that a property of a subterranean formation in which drill bit is positioned has changed based on one or more measurements, and, in response to determining that the subterranean formation has changed, automatically generating a drilling fluid adjustment plan based at least in part on one or more of a drilling fluid inhibition factor or a drilling fluid stability factor.

Embodiments of the disclosure include a system including a drilling rig including a drill string extending therefrom into a well, an electronic drilling recording system coupled to the drilling rig and configured to measure one or more parameters thereof. A drilling efficiency is directly measured or calculated based on the measured one or more parameters. The system includes one or more sensors configured to measure one or more properties of a drilling fluid circulating in the well, and a processor configured to perform operations, the operations including determining that the drilling efficiency is lower than expected, determining that a property of a subterranean formation in which drill bit is positioned has changed based on one or more measurements, and in response to determining that the subterranean formation has changed, automatically generating a drilling fluid adjustment plan based at least in part on one or more of a drilling fluid inhibition factor or a drilling fluid stability factor.

This summary introduces some of the concepts that are further described below in the detailed description. Other concepts and features are described below. The claims may include concepts in this summary or other parts of the description.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

Reference will now be made in detail to embodiments, examples of which are illustrated in the accompanying drawings and figures. In the following detailed description, numerous specific details are set forth in order to provide a thorough understanding of the invention. However, it will be apparent to one of ordinary skill in the art that the invention may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object could be termed a second object, and, similarly, a second object could be termed a first object, without departing from the scope of the invention. The first object and the second object are both objects, respectively, but they are not to be considered the same object.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. It will also be understood that the term "and/or" as used herein refers to and encompasses any possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Further, as used herein, the term "if" may be construed to mean "when" or "upon" or "in response to determining" or "in response to detecting," depending on the context.

Figure 1A:
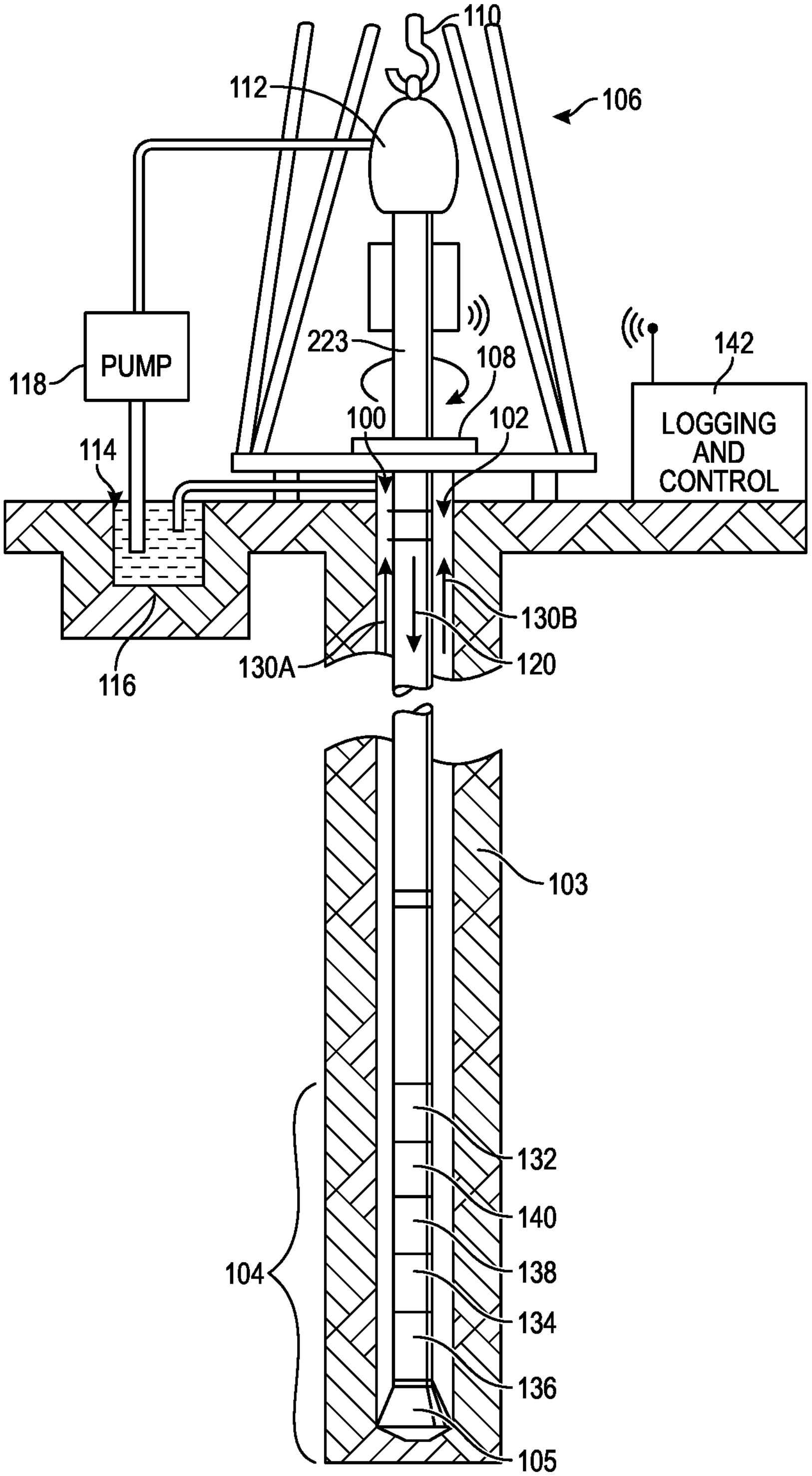
FIG. 1A illustrates a schematic side view of a wellsite system, according to an embodiment.

FIG. 1A illustrates a wellsite system according to examples of the present disclosure may be used. The wellsite can be onshore or offshore. In this example system, a drill string 100 is suspend in a bore 102 formed in subsurface formations 103. The drill string 100 has a bottom hole assembly (BHA) 104 which includes a drill bit 105 at its lower end. A surface system 106 includes platform and derrick assembly positioned over the borehole 102, the assembly including a rotary table 108, kelly (not shown), hook 110, and rotary swivel 112. The drill string 100 is rotated by the rotary table 108 energized by a driver, which engages the kelly (not shown) at the upper end of the drill string 100. The drill string 100 is suspended from the hook 110, attached to a traveling block (also not shown), through the kelly (not shown) and the rotary swivel 112 which permits rotation of the drill string 100 relative to the hook 110. A top drive system could be used instead of the rotary table system shown in FIG. 1.

In the illustrated example, the surface system 106 further includes drilling fluid or mud 114 stored in a pit 116 formed at the well site. A pump 118 delivers the drilling fluid to the interior of the drill string 100 via a port (not shown) in the swivel 112, causing the drilling fluid to flow downwardly through the drill string 100 as indicated by the directional arrow 120. The drilling fluid exits the drill string 100 via ports (not shown) in the drill bit 105, and then circulates upwardly through an annulus region between the outside of the drill string 100 and the wall of the borehole 102, as indicated by the directional arrows 130A and 130B. In this manner, the drilling fluid lubricates the drill bit 105 and carries formation cuttings up to the surface as it is returned to the pit 116 for recirculation.

The BHA 104 of the illustrated embodiment may include a measuring-while-drilling (MWD) tool 132, a logging-while-drilling (LWD) tool 134, a rotary steerable directional drilling system 136 and motor, and the drill bit 105. It will also be understood that more than one LWD tool and/or MWD tool can be employed, e.g., as represented at 138.

The LWD tool 134 is housed in a drill collar and can contain one or a plurality of logging tools. The LWD tool 134 may include capabilities for measuring, processing, and storing information, as well as for communicating with the surface equipment. In the present example, the LWD tool 134 may include one or more tools configured to measure, without limitation, electrical resistivity, acoustic velocity or slowness, neutron porosity, gamma-gamma density, neutron activation spectroscopy, nuclear magnetic resonance and natural gamma emission spectroscopy.

The MWD tool 132 is also housed in a drill collar and can contain one or more devices for measuring characteristics of the drill string and drill bit. The MWD tool 132 further includes an apparatus 140 for generating electrical power for the downhole system. This may typically include a mud turbine generator powered by the flow of the drilling fluid, it being understood that other power and/or battery systems may be employed. In the present embodiment, the MWD tool 132 may include one or more of the following types of measuring devices, without limitation: a weight-on-bit measuring device, a torque measuring device, a vibration measuring device, a shock measuring device, a stick slip measuring device, a direction measuring device, and an inclination measuring device. The power generating apparatus 140 may also include a drilling fluid flow modulator for communicating measurement and/or tool condition signals to the surface for detection and interpretation by a logging and control unit 142.

Figure 1B:
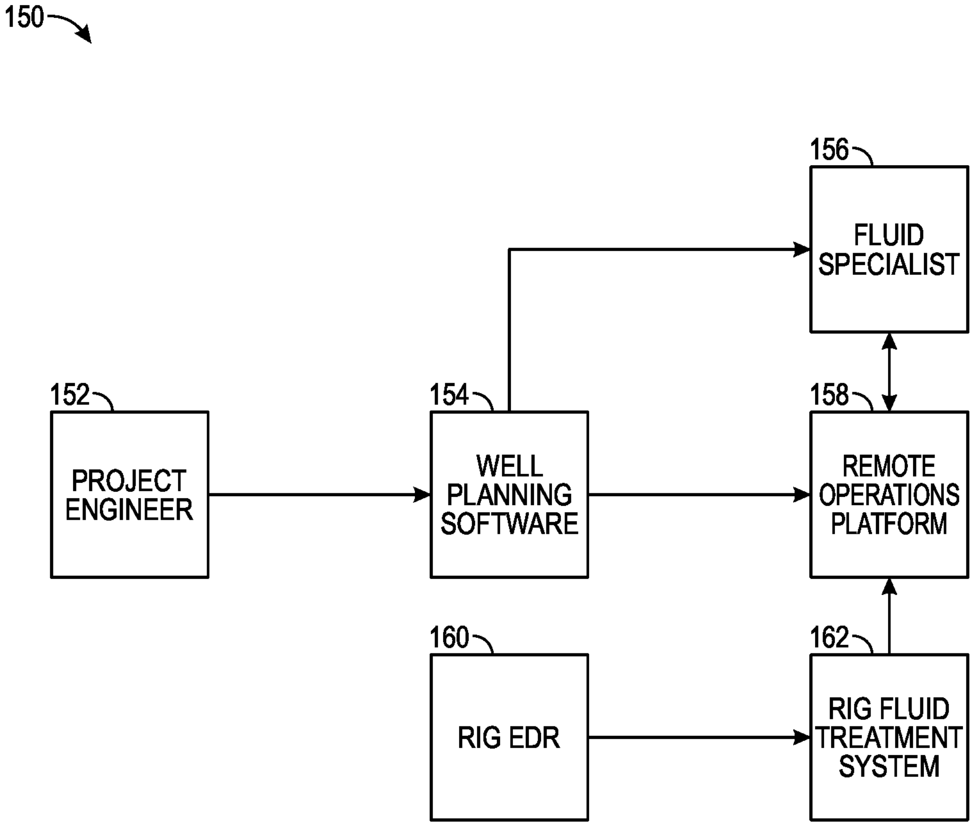
FIG. 1B illustrates a schematic view of an automatic system for controlling drilling fluid in a well, according to an embodiment.

FIG. 1B illustrates a system 150 for controlling drilling fluid operations on a drilling rig, such as the rig discussed above, according to an embodiment. As shown, a project engineer 152 may create a well plan for implementation by the drilling rig, e.g., using well planning software 154. The well planning software 154 may be a software program for fluid design and planning, including tools, libraries, and information that is tailored to assist in the well planning activity. Schlumberger's One-Trax Central well execution database and eLab field service laboratories requests and lab results repository are examples of libraries. In another embodiment, the well planning software 154 may be a well planning platform that allows engineers from different disciplines to collaboratively construct a well plan. Schlumberger's DrillPlan® software is one example of well planning software 154.

For example, as part of developing the well plan, the project engineer 152 may enter information that is used to construct a mud plan for the well being designed. This mud plan (whether by itself or along with other planning aspects for the well) may be captured in the well planning software 154 and transmitted to one or more recipients. In one embodiment, a human-readable version of the mud plan is created and given to a fluid specialist 156. The fluid specialist 156 may use the plan at the rig to manage and monitor the fluids being used during construction of the well.

The plan may also be sent to a remote operations system 158. In one embodiment, a machine-readable version of the plan is created and sent to the remote operations system 158. The machine-readable version of the plan may be a version that contains additional detail (and/or a different level of detail) suitable for use by a computer in monitoring or executing the plan. In one embodiment, the remote operations system 158 is hosted in a cloud computing environment such that it can be accessed remotely. Schlumberger's DrillOps® software is an example of software that includes a remote operations system 158.

In one embodiment, the remote operations system 158 extracts parameters from the drilling fluid program as set by the project engineer 152. The remote operations system 158 may extract these automatically from the drilling plan created by the well planning software 154. In another embodiment, a user may enter one or more of the parameters manually in the remote operations system 158.

During operations, data relevant to the construction of the well may be captured by the rig electronic data recorder (EDR) 160. The rig EDR 160 may send captured data to a rig fluid treatment system 162. In certain embodiments, the rig EDR 160 may send data to the remote operation system 158 as well.

The rig fluid treatment system 162 may be configured to measure drilling fluid properties. The rig fluid treatment system 162 may also be configured to automate one or more tasks related to fluid treatment and management. In one embodiment, the rig fluid treatment system 162 includes a rheometer. The rig fluid treatment system 162 may automate the rheometer to handle certain tasks and communicate real-time data to the remote operations system 158. The rig fluid treatment system 162 may measure the drilling fluid's rheology profile over various temperatures with gels, and density. The rig fluid treatment system 162 may timestamp and store rheology, gels, and density measurements and store them on the unit. The rig fluid treatment system 162 may also use WITS protocol to transmit the measurements. In one embodiment, the rig fluid treatment system 212 may be or include Schlumberger's RheoProfiler automated rheometer.

The remote operations system 158 may receive real-time data from the rig fluid treatment system 162, the rig EDR 160, and/or other sources. The remote operations system 158 may receive the real-time data from the rig fluid treatment system 162 directly; in other embodiments, the data is sent via one or more intermediary devices such as an Internet of Things (IoT) Gateway or other device on the well site. The fluid specialist 156 may, in certain embodiments, also send information to the remote operations system 158. For example, the fluid specialist 156 may complete one or more digital forms about the operations, and the forms may then be sent to the remote operations system 158.

The remote operations system 158 may use data from the disparate sources to provide insights and information to the fluid specialist 156, which may be the same individual or a different human at a different location. For example, the fluid specialist 156 may be located in a remote support center and monitors data about fluids from multiple wells being drilled. In such an embodiment, the fluid specialist 156 may receive one or more recommendations from the remote operations system 158. For example, if two fluid specialists 156 are employed, one may be local and one remote, with communication therebetween provided via the remote operations system 158. In one embodiment, the fluid specialist 156 may initiate one or more actions at the location of the rig from the remote center where the fluid specialist 156 is located. In such an embodiment, the rig fluid treatment system 162 may receive the commands and execute the instructions. The rig fluid treatment system 162 may require that the (local) fluid specialist 156 confirm and approve the instructions from the (remote) fluid specialist 156 before execution.

In one embodiment, the remote operations system 158 extracts the parameters from the drilling plan provided by the well planning software 154 as described above. The remote operations solution may receive the real-time measurements and compare the actual values as represented by the real-time measurements with the planned values in the plan provided by the project engineer 152. The remote operations system 158 may provide visualizations of how the actual values and the expected values compare. The remote operations system 158 may also provide alerts and alarms when one or more of the values deviate from the plan.

Figure 2A:
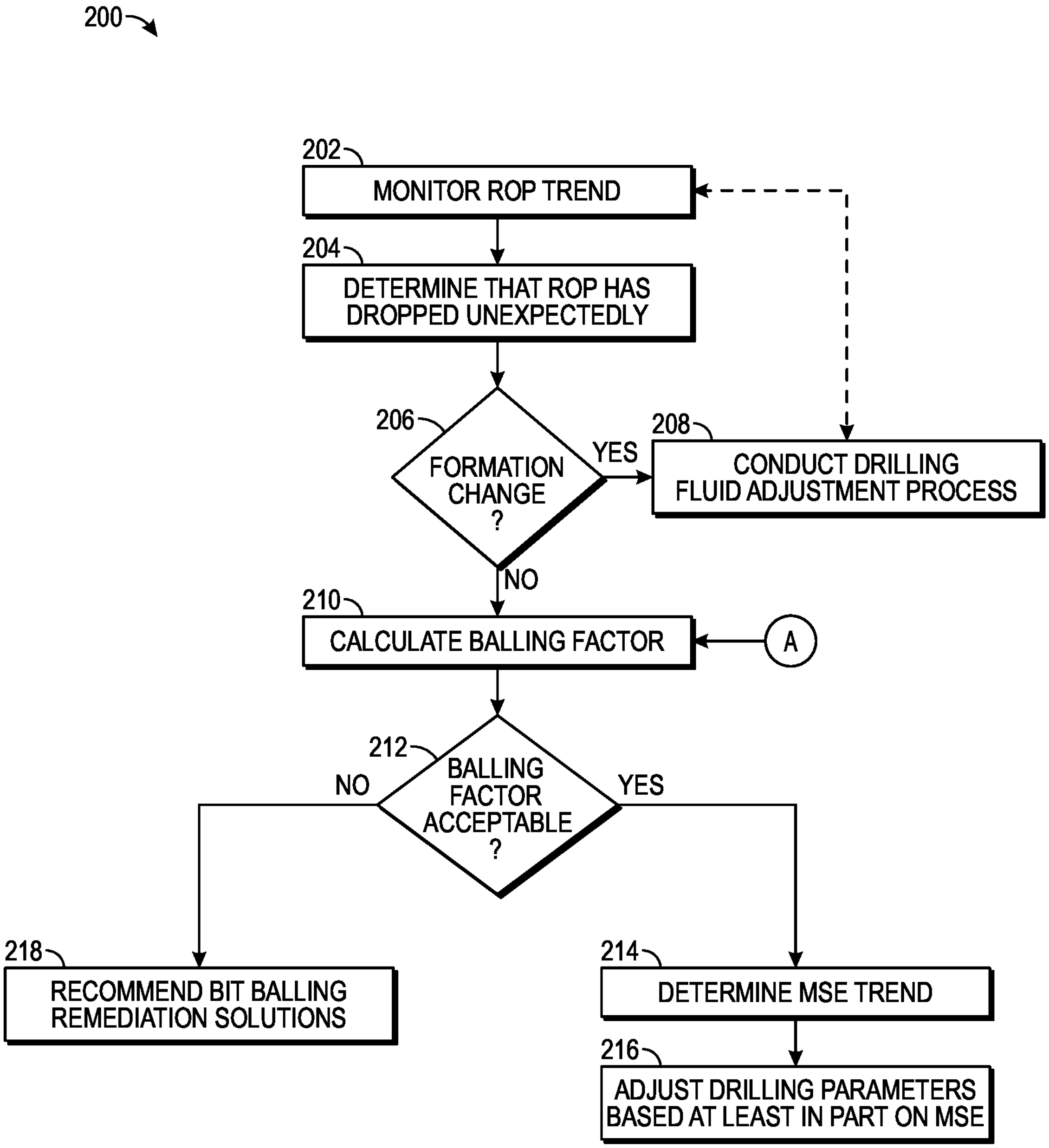
FIGS. 2A, 2B, and 2C illustrate a flowchart of a method for controlling drilling fluid in a well, according to an embodiment.
Figure 2B:
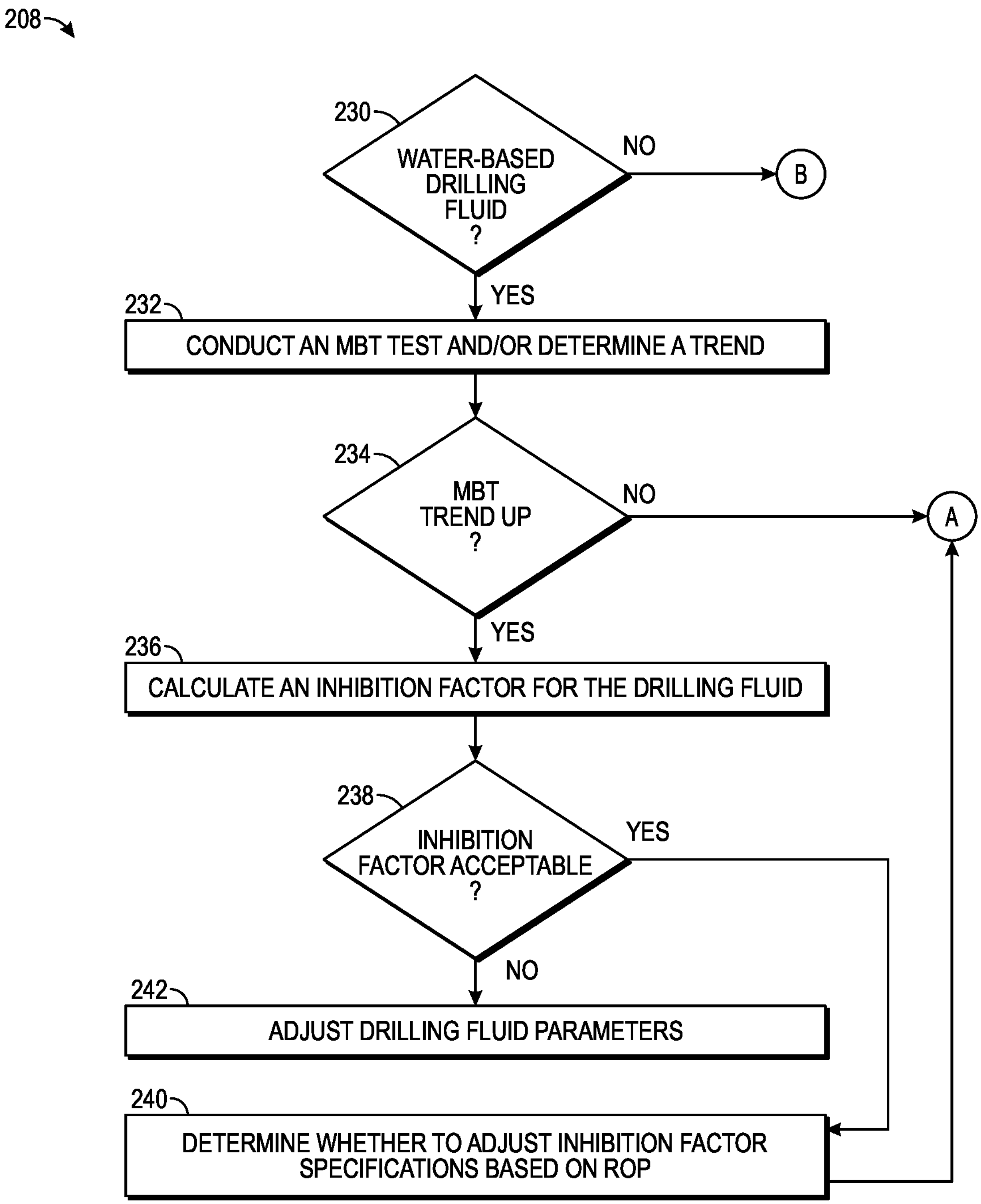
Figure 2C:
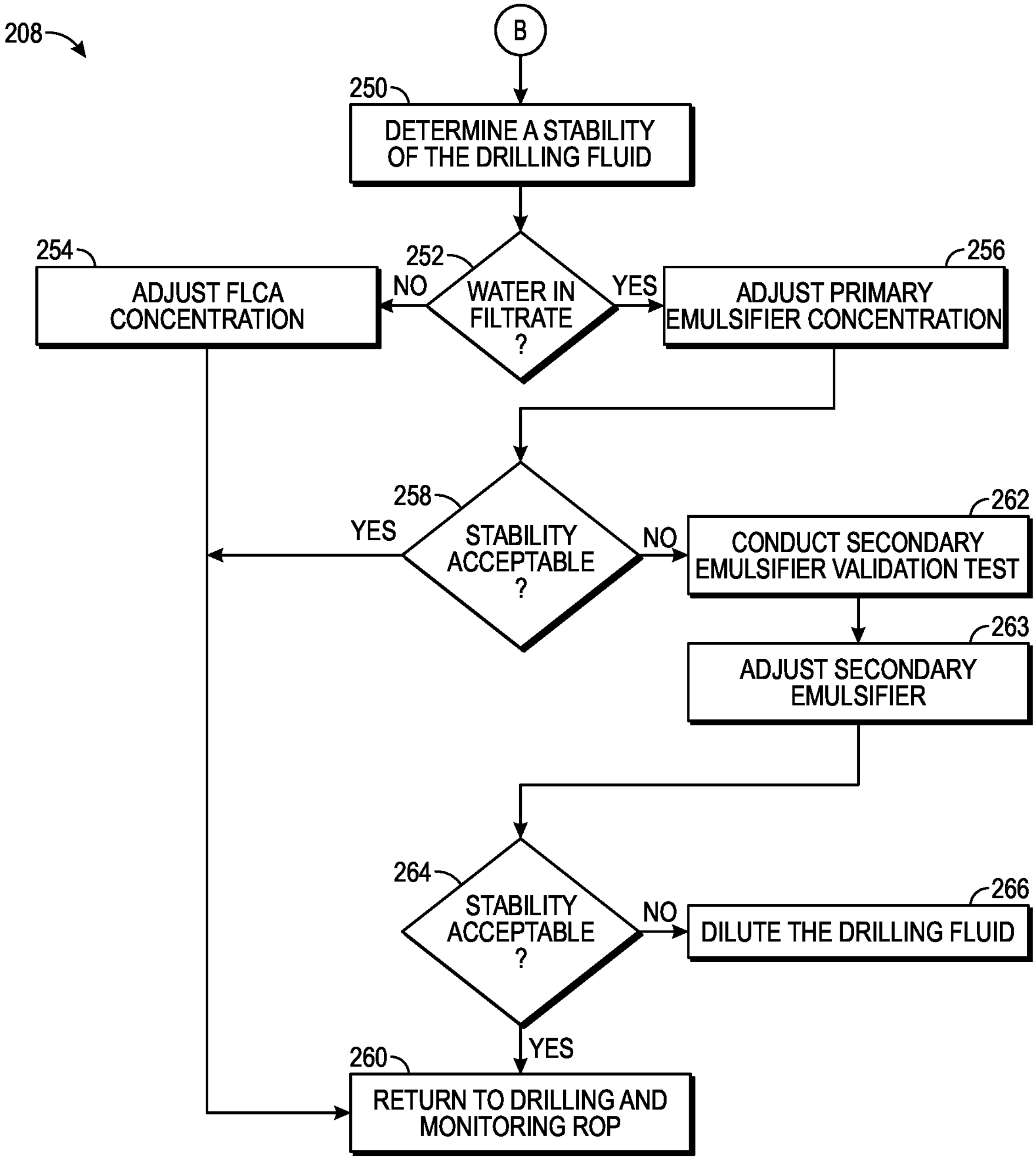

FIGS. 2A, 2B, and 2C illustrate a flowchart of a method 200 for managing drilling fluid in a well, using a drilling rig, according to an embodiment. In at least some embodiments, the method 200 may be executed using the remote operations system 158, the rig EDR 160, and/or the rig fluid treatment system 162. In at least some embodiments, the method 200 may be executed at least partially by a processor exercising control over at least a portion of the system 150, e.g., operable to receiving sensor inputs, make recommendations to a user (e.g., the fluid specialist 156), and/or to directly implement activities for adjusting and maintaining fluid specifications. In some embodiments, execution of the method 200 may thus provide a drilling fluid analyzer and/or adjustment engine, which may supplant one or more of the fluid specialists 156 generally employed at a rig. Further, it will be appreciated that the elements of the method 200 may be performed in the order presented, in any other order, in parallel, in multiple parts, in combination, etc., without departing from the scope of the present disclosure.

The method 200 may include monitoring various inputs, e.g., from the rig EDR 160 and/or other sources. The rig EDR 160 may provide various measurements, including drilling parameter values, which may permit a calculation and/or direct measurement of drilling efficiency, e.g., rate of penetration (ROP) of the drilling rig to be fed into the method 200 as input, received at 202. The ROP is generally a measure of the speed at which a drill bit is advanced into a well, that is, the rate at which the borehole is lengthened. Various statistical metrics may be developed and monitored based on the ROP measurement/calculations, such as ROP trends.

The ROP (or another drilling efficiency measure) may serve as a trigger in the method 200. For example, the trigger may be that, at some point, the ROP may drop unexpectedly, as at 204. This may be considered undesirable, as it represents, potentially, not only inefficiency and a slowing of the drilling process, but also the potential for unfavorable drilling conditions in the well, which could become hazardous, or at least call for expensive remediation procedures, if not corrected in a timely fashion. By contrast, some drops in ROP are expected, such as during make-up (addition) of drill pipes to the drill string in order to extend the drill string—this incurs a pause in the drilling process to thread the new pipes onto the string.

When unexpected drops in ROP (e.g., beyond a threshold amount from the expected ROP based on the trend), the method 200 may determine whether there has been a formation change, as at 206. As mentioned above, the appropriate drilling fluid may be at least partially a function of formation properties. For example, highly porous formations may require a different bottomhole pressure (e.g., provided by adjusting density of the drilling fluid) than less porous formations. This is merely one, simplistic example, however, and one of ordinary skill in the art will recognize that there are a host of different factors that can affect selection of drilling fluid parameters. Whether a formation change has occurred may be determined by logging and/or measurement while drilling equipment that may be positioned at or near the bottomhole assembly, which may function to determine formation properties.

If the formation properties are not consistent with the drilling plan (e.g., DDP or digital drilling plan), e.g., representing a change in the formation from expectations built into the well plan, the method 200 may proceed to compensating by conducting an at least partially automated drilling fluid adjustment process, as at 208. This process 208 will be discussed in greater detail below. The line extending from the box 208 to the initial ROP measurement/calculation box 202 should be noted, as this represents a feedback function that will be discussed in greater detail below as well.

If the formation properties have not changed (or are expected as per the DDP), the method 200 may proceed to detecting if bit balling is occurring instead. Briefly, bit balling occurs when clay in the formation attaches to the drill bit and impedes the cutting ability of the bit. Normally, drilling fluid is employed to keep the drill bit clear of such clay, but balling may occur in various circumstances and may be avoided. For example, a bit balling factor may be calculated, as at 210. The bit balling factor may represent a likelihood that bit balling is occurring and/or the impact it is having on the drilling operation, and may be calculated based on a variety of factors, such as circulating drilling fluid properties and/or trends thereof, EDR measurements (e.g., torque, weight-on-bit or WOB, drill string revolution per minute or RPM, pick up/slack off weights, etc.), drilling fluid additives history, drilling fluid solids content, drilling fluids particle size distribution, etc.

The bit balling factor that is calculated may then be compared to a specification (e.g., upper or lower limit) to determine if it is acceptable, as at 212. If the bit balling factor is within specification, it may indicate that bit balling is not affecting ROP, or at least not explaining the drop in ROP that has been detected. Accordingly, the source of the ROP drop may be considered to be found in the drilling parameters. Thus, for example, mechanical specific energy (MSE) trends or other metrics may be determined, as at 214, and drilling parameters (e.g., speed, weight on bit, etc.) may be adjusted accordingly, e.g., within a pore pressure fracture gradient window, as at 216.

If the bit balling factor is not within specification, it may indicate that bit balling is occurring. As such, the method 200 may include recommending and/or automatically initiating bit balling remediation processes, as at 218. Such bit balling remediation processes may include pumping a soaking pill, conducting a wiper trip, or pulling the BHA out of the well and reconfiguring the BHA. The bit balling factor specification may be predetermined and/or dynamically set in response to ROP calculated at least partially as a function of bit balling factor. That is, a bit balling factor specification may be modified depending on the impact that a measured bit balling factor being near the end range of the specification has on the ROP. For example, if an out-of-specification bit balling factor has no or little impact on ROP, the specification may be expanded, or if an in-specification bit balling factor causes a drop in ROP, the specification may be narrowed. This may be a manual trial-and-error process, or may rely on trends recognized by a computing device (e.g., via machine learning).

FIG. 2B illustrates a flowchart of a portion of the drilling fluid adjustment process 208 in greater detail, according to an embodiment. The drilling fluid adjustment process may be configured to generate a drilling fluid adjustment plan, which may be implemented by a user, e.g., a display of recommendations, alerts, etc. In other embodiments, the drilling fluid adjustment process may automatically implement at least a portion of the drilling plan, in addition to generating the drilling plan.

The drilling fluid adjustment process 208 may begin by determining the general type of drilling fluid that is being circulated, as at 230. There are generally two types of drilling fluid, aqueous (water-based) drilling fluid and non-aqueous (hydrocarbon- or "oil"-based) drilling fluid. The two different types of fluids have different properties, and thus may be treated differently in the drilling fluid adjustment process 208. For example, water-based drilling fluids often have a large amount of suspended solids there, while oil-based drilling fluids often have multiphase combinations of hydrocarbons-based continuous phase and an aqueous internal phase that are emulsified together, e.g., using various surfactants.

If the drilling fluid is water-based, the process 208 may proceed to determining reactivity, e.g., conducting methylene blue test (MBT) and/or calculating a trend in MBT test results, as at 232. An MBT test is a test to determine the amount of clay-like materials in a water-based drilling fluid based on the amount of methylene blue dye absorbed by a sample. An increasing (or otherwise relatively high result for a) MBT test, as determined at 234, may represent high reactivity of the clay in the formation with the drilling fluid. That is, the clay is becoming hydrated by the drilling fluid, which may impede the drilling process. By comparison, if the MBT test is not high or trending upwards (or reactivity is otherwise determined to be relatively low or not the cause of the reduced ROP), the drilling fluid may not be adjusted. As such, the method 200 may return to block 210 at 'A', as indicated in FIGS. 2A and 2B.

Inhibitors may be employed to avoid such reactivity between the drilling fluid and the clay. Thus, if reactivity is up (as indicated, e.g., by the MBT test), the process 208 may proceed to determining whether inhibition is within an acceptable range. For example, an inhibition factor may be calculated, as at 236, e.g., based on one or more of circulating drilling fluid properties trends, EDR channels (torque, weight-on-bit or WOB, drill string revolution per minute or RPM, pick up/slack off weights, etc.), drilling fluids products additions history, solids content, drilling fluids particle size distribution, or any combination thereof.

The inhibition factor that was calculated may then be compared to a specification, to determine whether the inhibition factor is acceptable, as at 238. If the inhibition factor is acceptable, the general process 208 may be to check for balling, as at circle 'A', leading to block 210 of FIG. 2A. However, as noted above, a feedback loop may be employed as part of the process 208. In this case, if the ROP is consistently lower than expected, but the inhibition factor is within specification but, e.g., marginal or near the end of the specification, the process 208 may determine whether to adjust the inhibition factor specification based on the ROP, as at 240. This may, accordingly, be an iterative process, whereby, for example, the process keeps track of the inhibition factor and the ROP in order to determine, e.g., dynamically, automatically, and/or by human intervention, whether to adjust the inhibition factor specification. Further, a computing device may track and adjust the specifications, e.g., using machine learning.

If the inhibition factor is not acceptable, the drilling fluid parameters may be adjusted, e.g., as part of or in response to a drilling fluid adjustment plan. This may be accomplished by adding barite, inhibitors, etc. A prescribed addition of amounts and types of additives may be recommended or automatically initiated. Further, the addition may be iterative, and, as part of adjusting the drilling fluid parameters at 242, the process 208 may loop back to taking new MBT tests at 232 and recalculating the inhibition factor 236 to determine if the inhibition factor is now within specification at 238. Moreover, a history log may be updated as additives are mixed into the drilling fluid, and subsequent drilling fluid additions may at least partially rely on the history to determine what additives may be most efficiently used to result in a desired inhibition factor and, thus, mitigate the ROP reduction. In other words, in some embodiments, the drilling fluid additives history may specify a timeline of the addition of different additives (e.g., emulsifiers, surfactants, barite, other components) to the drilling fluid. The drilling fluid adjustment plan may be selected so as to account for such timeline, e.g., by deciding to or deciding not to add a certain component based on when it was last added (e.g., relative to other components being added).

Returning to block 230, if water-based drilling fluid is not being used, i.e., oil-based drilling fluid is being circulated in the well instead, the process 208 proceeds to 'B'. FIG. 2C illustrates a flowchart of another part of the process 208, starting at 'B', according to an embodiment. As mentioned above, oil-based drilling fluid may include an emulsification of two or more immiscible fluids, such that the drilling fluid is substantially homogeneous. The ability of the drilling fluid to maintain such homogeneity, without substantial phase separation, may be referred to as the "stability" of the drilling fluid. If the stability is low, the fluid viscosity may be impacted as the different phases may begin to act separately and potentially result in drill solids losing their acquired oil wet state and turn into an undesirable water wet state (i.e. sticky if the clays are reactive), which may cause issues in the drilling process, leading to, for example, unexpected drops in ROP.

Accordingly, the process 208 may include determining a stability of the drilling fluid, as at 250. The stability of the drill fluid may be quantified by calculation of a stability factor. The stability factor may at least partially be a function of one or more of circulating drilling fluid properties trends, EDR channels (weight-on-bit or WOB, drill string revolution per minute or RPM, torque, pick up/slack off weights, etc.), product addition history, solids content, particle size distribution, or a combination thereof.

The process 208 may then conduct a high-temperature, high-pressure fluid loss trend, which may determine whether there is water in the filtrate, as at 252. If there is not water in the filtrate, e.g., the water is emulsified in the oil of the drilling fluid, the process 208 may proceed to delivering a treatment recipe to adjust fluid loss control agent (FLCA) concentration, e.g., as part of the drilling fluid adjustment plan and/or adjusting the FLCA concentration automatically, as at 254. Otherwise, a primary emulsifier may be adjusted (or planned for adjustment), as at 256. Drilling may then recommence with ROP being monitored, as at 260.

After the primary emulsifier is adjusted, the stability factor may again be determined and compared to a specification, as at 258. If the stability factor is now in specification, the process 208 may proceed to 260, where the process 208 returns to the initial drilling protocol, in which ROP is monitored for unexpected drops, as shown in FIG. 2C at 260 (and also 202 of FIG. 2A). The stability factor specification may be predetermined and/or dynamically set in response to ROP calculated at least partially as a function of the stability factor. That is, a stability factor specification may be modified depending on the impact that a calculated stability factor being near the end range of the specification has on the ROP. For example, if an out-of-specification stability factor has no or little impact on ROP, the specification may be expanded, or if an in-specification stability factor causes a drop in ROP, the specification may be narrowed. This may be a manual trial-and-error process, or may rely on trends recognized by a computing device (e.g., via machine learning).

If adjusting the primary emulsifier was not successful in bringing the stability factor into specification, one or more secondary emulsifier concentrations may be adjusted. For example, a secondary emulsifier validation test may be conducted, as at 262. This test may specify a concentration and/or type of emulsifier for use, or confirm suitability for use of a proposed secondary emulsifier. The secondary emulsifier concentration may then be adjusted, as at 263, based on the secondary emulsifier validation test, and the stability factor again checked against the specification, as at 264. This process may be repeated for additional secondary emulsifiers, in some embodiments, e.g., in series with subsequent stability factor recalculation and comparison to specification.

If adjusting the emulsifiers is not successful, the drilling fluid may be diluted with fresh ("virgin") drilling fluid, as at 266. Such dilution may proceed according to a schedule, e.g., until the stability factor is brought to within specification. If, during the process of adjusting the primary and/or secondary emulsifiers is successful, and/or after sufficiently diluting the drilling fluid (if called for), the process 208 may return to drilling and monitoring ROP at 260.

Adjustments to the emulsifiers may be based at least partially on a drilling fluid additives history, which may be tracked as part of the process 208. As noted above, in some embodiments, the drilling fluid additives history may specify a timeline of the addition of different additives (e.g., emulsifiers, surfactants, barite, other components) to the drilling fluid. The drilling fluid adjustment plan may be selected so as to account for such timeline, e.g., by deciding to or deciding not to add a certain component based on when it was last added (e.g., relative to other components being added).

Accordingly, it will be seen that embodiments of the method 200 may provide for automatic diagnosis and treatment of drilling fluid conditions that lead to reduction in drilling efficiency (e.g., ROP). For water-based drilling fluid, such ROP reductions may be caused by insufficient inhibition and/or excessive reactivity with the clay in the formation, which may be mitigated as discussed above. Further, in oil-based drilling fluid applications, the stability may be the cause of the diminished ROP, and thus the method 200 may recommend or initiate actions (generally the modification of one or more emulsifier concentrations) to increase stability. In either case, adjustment of the drilling fluid may not be called for if bit balling is the cause of the ROP reduction, and the method 200 may automatically account for such possibility. Further, the method 200 may not be based solely on static rules, but may dynamically update the various specifications, e.g., if ROP is consistently lower than expected and certain factors are near to their respective threshold, as this may indicate the threshold is positioned incorrectly.

Figure 3:
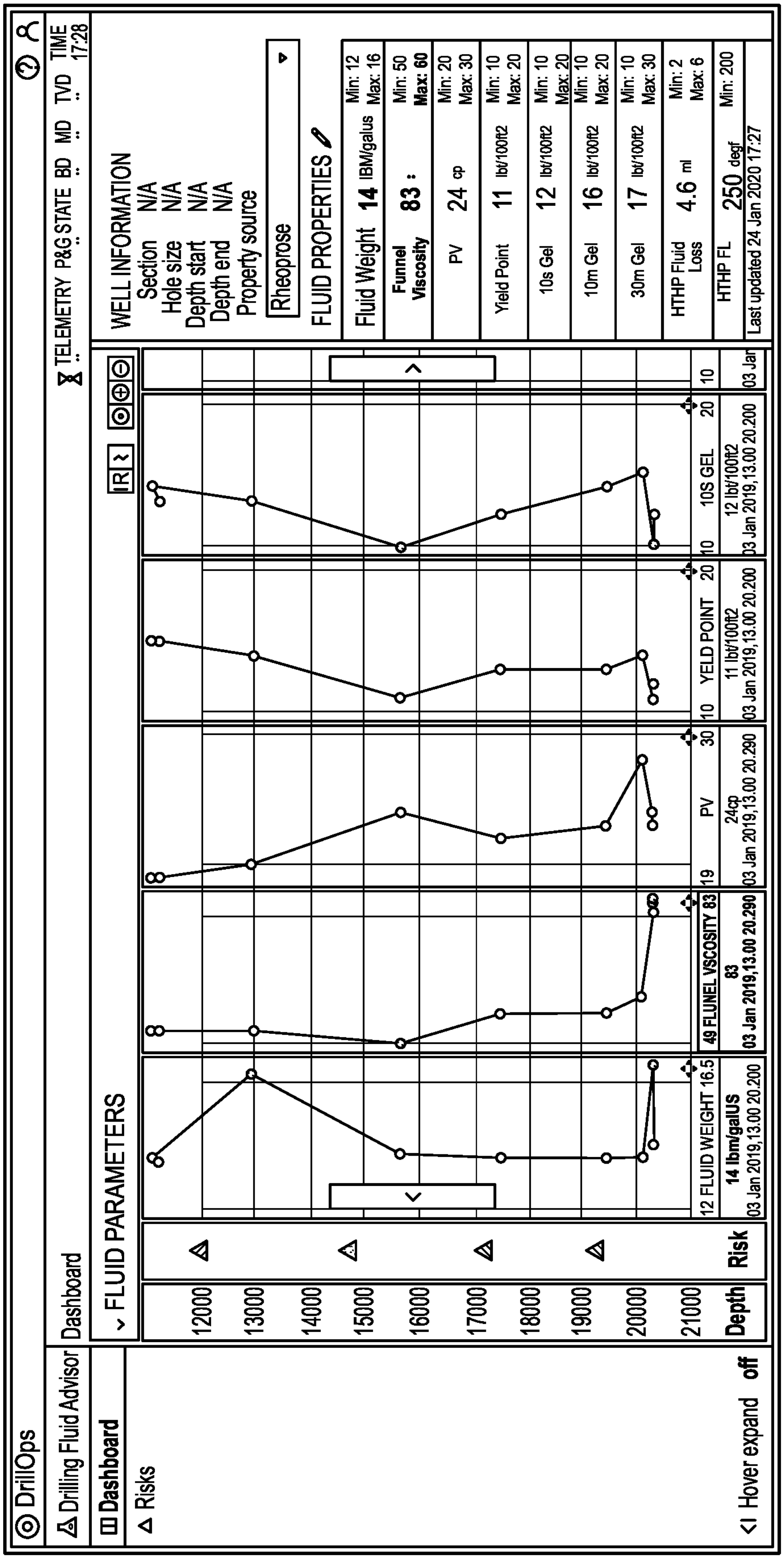
FIG. 3 illustrates a user interface provided by a remote operations system, according to an embodiment.

FIG. 3 illustrates one embodiment of a user interface the remote operations system 158 may provide. In FIG. 3, the fluid properties as received from the wellsite are displayed. As discussed above, these values may come from the rig fluid treatment system 162 directly, from the fluid specialist 156 at the rig site, or a combination thereof.

The fluid parameters from the well plan may be displayed as acceptable ranges representing the width of the columns. For example, the parameters for the fluid weight shown in FIG. 3 may originate from the plan. The far left may represent the low end of the acceptable range, while the far right of the column may represent the high end of the acceptable range. The y-axis may represent the depth of the well at the particular point.

As real-time data for the values comes into the remote operations system 158, the value may be plotted for each parameter at the depth at the time of measurement. The black dots in FIG. 3 represent the discrete measured values. In one embodiment, when the measurement falls outside the acceptable range defined in the plan, the dot is presented in red. In one embodiment, when the latest measurement is outside the acceptable range, the dot and the number at the bottom representing the latest measurement are both presented in red. For example, the funnel viscosity in FIG. 3 represents such an embodiment.

Figure 4:
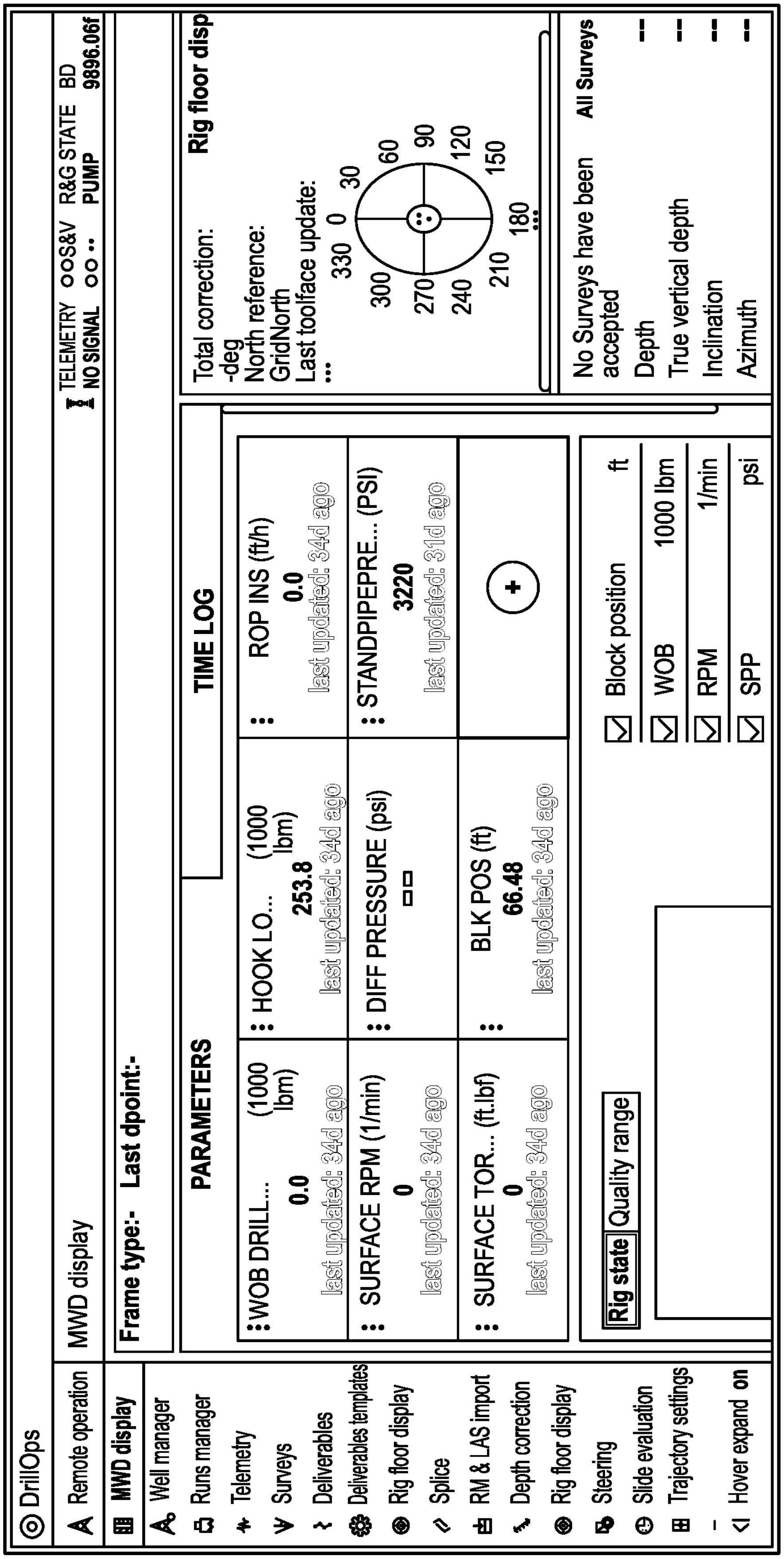
FIG. 4 illustrates another aspect of the user interface, showing a display of rig state, according to an embodiment.

The remote operations system 158 may also highlight the risks associated with the plan at particular depths. In one embodiment, where the risks are elevated through a certain depth, a risk indicator is shown in the "Risk" column as shown in FIG. 3. Colors, symbols, or other approaches may be used to indicate different levels of risk. As shown in FIG. 4, the remote operations system 158 may also present information relating to the rig state.

The disclosed solution may provide a web-based application that receives fluid measurement information from the wellsite and shows whether the measurements are within acceptable parameters or not. The measurements can come from software/hardware at the wellsite, with the planned parameters coming from planning software. The solution may be deployed as part of a remote operations monitoring solution to enable monitoring aspects of drilling (including fluids) at multiple locations. The solution may also allow users to update the planned parameters if, due to changing conditions, the parameters inputted at the planning stage need to be changed or updated as part of a replanning/re-evaluation process.

Real-time measurements may come in at various intervals. In one embodiment, measurements are made every 30 minutes. In another embodiment, the measurements are made less frequently—particularly where the measurements need to be made manually. In one embodiment, the measurements are made between 2-5 times a day. In this instance, real-time means measurements made during the construction of the well and sent to the remote operations system 158 during the construction of the well (as opposed to measurements that are gathered during construction and sent at a later time, such as when the construction of the well is complete, when a device/report/etc. happens to be entered into a system, etc.). Given issues with connectivity and bandwidth limitations, the measurements may not necessarily be sent at the exact moment they are made; there may be a lag between measurement and transmission. Real-time, as used herein, is intended to cover such cases unless noted otherwise.

The automated drilling fluids management system may thus include a drilling fluids analyzer that can measurement one or more physicochemical properties of the drilling fluid. For example, it may measure rheology, density, gel strength, fluid loss, conductivity, electrical stability, oil fraction, water fraction, oil-water ratio, solids content, chlorides, alkalinity, or other.

The automated drilling fluids management system may also include a digitized drilling plan that includes a fluids program and depth-based schedule, along with other rig activities pertaining to drilling fluids. It may include a connection to the rig EDR that makes current and historical drilling rig parameters from rig instrumentation available.

The automated drilling fluids management system may compare the measurement output from the fluid analyzer to the digital drilling program. It may also determine the product additions and treatments available to condition the fluid to the required specifications. It may also be configured to communicated with a control system for controlling product additions and solids control treatment equipment that is fluidly coupled to the drilling fluid system.

In certain embodiments, the system is linked to a digitized fluid product inventory. The system may make treatment recommendations based on products available on the rig. The system may also have access to cost information. The system may make treatment recommendations based on cost. In one embodiment, the system creates multiple alternative treatment recommendations based on different optimizations. The system may present the results to the user and allow the user to select a treatment based on the goals and objectives of the user.

The system may action treatments or automate one or more aspects that facilitate the treatment. In one embodiment, the system may turn pumps on or off, actuate valves, and engage equipment to facilitate the treatment. The system may take actions with or without human oversight.

In one embodiment, the system looks ahead at the digitized drilling plan and forecasts changes required in the drilling fluid properties as indicated in the plan. The system may execute changes in fluid parameters and properties such as volume and composition based on the plan.

The system may further be configured to monitor a digitized fluid product inventory for the wellsite. The system may recommend orders, or automatically order, products for delivery to the well site for consumption. In one embodiment, the system accounts for travel time and location of the fluids and the well plan such that it places or recommends orders based on the future needs of the fluid specialist and system based on the plan.

The system may further be connected to a digitized database of recorded process and instrumentation data and analysis of prior wells. The system may use machine learning to identify previous drilling events and risks encountered in offset wells such as stuck pipe, fluid losses, poor hole cleaning, gas or water influxes, low ROP, and others. The system may associate one or more drilling risks and events with the operational and fluid properties for the well at the time of the risk and/or the times immediately before and after the risk. The system may monitor for operational parameters received from the EDR, combined with the fluid properties, that were associated with risks in previous wells. If the same or similar conditions occur during execution of the well under construction, the system may notify one or more personnel at the wellsite, in remote locations, or both. The system may be further configured to execute one or more corrective actions to reduce the risk.

The system may further use machine learning algorithms and the digitized fluid product inventory to automatically order products for delivery to the wellsite per the plan, to mitigate unforeseen drilling issues such as losses, or both. The system may allow the automated behaviors and recommendations to be monitored, altered, or over-ridden by a person monitoring the well—whether remote or in person. In one embodiment, the system is an online system that continually updates machine learning models as new data becomes available.

In one or more embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Figure 5:
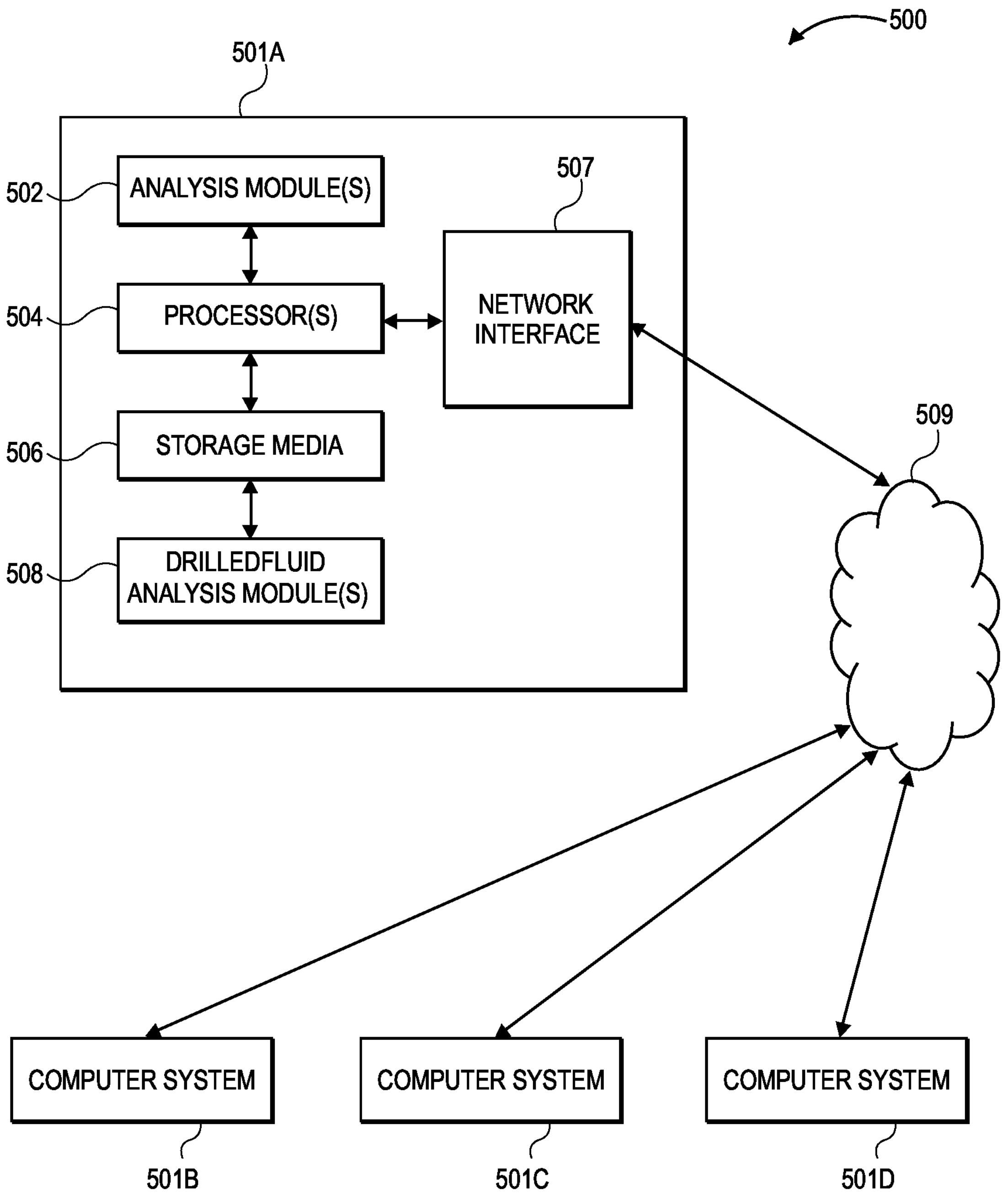
FIG. 5 illustrates a schematic view of a computing system, according to an embodiment.

In some embodiments, any of the methods of the present disclosure may be executed by a computing system. FIG. 5 illustrates an example of such a computing system 500, in accordance with some embodiments. The computing system 500 may include a computer or computer system 501A, which may be an individual computer system 501A or an arrangement of distributed computer systems. The computer system 501A includes one or more analysis module(s) 502 configured to perform various tasks according to some embodiments, such as one or more methods disclosed herein. To perform these various tasks, the analysis module 502 executes independently, or in coordination with, one or more processors 504, which is (or are) connected to one or more storage media 506. The processor(s) 504 is (or are) also connected to a network interface 507 to allow the computer system 501A to communicate over a data network 509 with one or more additional computer systems and/or computing systems, such as 501B, 501C, and/or 501D (note that computer systems 501B, 501C and/or 501D may or may not share the same architecture as computer system 501A, and may be located in different physical locations, e.g., computer systems 501A and 501B may be located in a processing facility, while in communication with one or more computer systems such as 501C and/or 501D that are located in one or more data centers, and/or located in varying countries on different continents).

A processor can include a microprocessor, microcontroller, processor module or subsystem, programmable integrated circuit, programmable gate array, or another control or computing device.

The storage media 506 can be implemented as one or more computer-readable or machine-readable storage media. Note that while in the example embodiment of FIG. 5 storage media 506 is depicted as within computer system 501A, in some embodiments, storage media 506 may be distributed within and/or across multiple internal and/or external enclosures of computing system 501A and/or additional computing systems. Storage media 506 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 500 contains one or more drilling fluid analysis module(s) 508. In the example of computing system 500, computer system 501A includes the drilling fluid analysis module 508. In some embodiments, a single drilling fluid analysis module may be used to perform some or all aspects of one or more embodiments of the methods. In alternate embodiments, a plurality of drilling fluid analysis modules may be used to perform some or all aspects of methods.

It should be appreciated that computing system 500 is only one example of a computing system, and that computing system 500 may have more or fewer components than shown, may combine additional components not depicted in the example embodiment of FIG. 5, and/or computing system 500 may have a different configuration or arrangement of the components depicted in FIG. 5. The various components shown in FIG. 5 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the invention.

Various interpretations, models, and/or other interpretation aids may be refined in an iterative fashion; this concept is applicable to embodiments of the present methods discussed herein. This can include use of feedback loops executed on an algorithmic basis, such as at a computing device (e.g., computing system 500, FIG. 5), and/or through manual control by a user who may make determinations regarding whether a given step, action, template, model, or set of curves has become sufficiently accurate for the evaluation of the subsurface three-dimensional geologic formation under consideration.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods are illustrated and described may be re-arranged, and/or two or more elements may occur simultaneously. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method for controlling drilling fluid properties, the method comprising:

receiving one or more measurements representing a drilling efficiency of a drilling rig including a drill bit deployed into a well, the drilling rig circulating a drilling fluid in the well;

determining that the one or more measurements are lower than expected;

determining that a property of a subterranean formation in which the drill bit is positioned has changed based on one or more measurements; and in response to determining that the property of the subterranean formation has changed:

determining that the drilling fluid is a non-aqueous drilling fluid;

calculating a stability of the non-aqueous drilling fluid;

determining that the stability is not acceptable;

conducting a secondary emulsifier pilot test to determine a secondary emulsifier, determining an additive history representing a timeline of fluid additives added to the drilling fluid; and the drilling rig automatically performing a drilling fluid adjustment to the drilling fluid being circulated by the drilling rig, the drilling fluid adjustment being based at least in part on one or more of a drilling fluid inhibition factor or a drilling fluid stability factor, wherein the drilling fluid adjustment includes one or more emulsifier concentration changes to attempt to increase the stability of the non-aqueous drilling fluid, and wherein the drilling fluid adjustment is further based at least in part on the additive history.

2. The method of claim 1, further comprising:

determining that bit balling, one or more drilling parameters, or both are causing the one or more measurements representing drilling efficiency to be lower than expected; and performing one or more bit balling remediation actions, changing one or more drilling parameters, or both.

3. The method of claim 1, further comprising:

conducting a reactivity test for the drilling fluid; and determining that a reactivity test result, a trend of reactivity test results, or both are outside of a design specification, wherein the drilling fluid adjustment is further based on the determining that the reactivity test result, the trend of reactivity test results, or both are outside of a design specification.

4. The method of claim 3, further comprising:

in response to the determining that the reactivity test is outside of the design specification, determining that the drilling fluid inhibition factor is out of specification; and the drilling fluid adjustment comprises returning the drilling fluid inhibition factor to within the specification.

5. The method of claim 4, further comprising:

in response to the determining that the reactivity test is outside of the design specification, determining that the drilling fluid inhibition is not out of specification; and in response to the determining that the drilling fluid inhibition is not out of specification:

determining that bit balling is occurring in the drill bit; and automatically initiating one or more bit balling remediation processes.

6. The method of claim 4, further comprising adjusting a drilling fluid inhibition specification based at least in part on a combination of the drilling efficiency and the drilling fluid inhibition factor.

7. The method of claim 1, further comprising:

determining that there is not water in a filtrate collected during a high pressure high temperature test, wherein the drilling fluid adjustment comprises an adjustment to a fluid loss control agent concentration in response to the determining that there is not water in the filtrate.

8. A computing system, comprising:

one or more processors; and a memory system including one or more non-transitory computer-readable media storing instructions that, when executed by at least one of the one or more processors, cause the computing system to perform operations, the operations comprising:

receiving one or more measurements representing a drilling efficiency of a drilling rig including a drill bit deployed into a well, the drilling rig circulating a drilling fluid in the well;

determining that the one or more measurements are lower than expected;

determining whether a property of a subterranean formation in which the drill bit is positioned has changed based on one or more measurements; and in response to determining that the property of the subterranean formation has changed:

determining that the drilling fluid is a non-aqueous drilling fluid;

calculating a stability of the non-aqueous drilling fluid;

determining that the stability is not acceptable;

conducting a secondary emulsifier pilot test to determine a secondary emulsifier, determining an additive history representing a timeline of fluid additives added to the drilling fluid; and the drilling rig automatically performing a drilling fluid adjustment to the drilling fluid being circulated by the drilling rig, the drilling fluid adjustment being based at least in part on one or more of a drilling fluid inhibition factor or a drilling fluid stability factor, wherein the drilling fluid adjustment includes one or more emulsifier concentration changes to attempt to increase the stability of the non-aqueous drilling fluid, and wherein the drilling fluid adjustment is further based at least in part on the additive history.

9. The computing system of claim 8, wherein the operations further comprise:

determining that the property of the subterranean formation has not changed;

determining that bit balling, one or more drilling parameters, or both are causing the one or more measurements representing drilling efficiency to be lower than expected; and performing one or more bit balling remediation actions, changing one or more drilling parameters, or both.

10. The computing system of claim 8, wherein the operations further comprise:

determining that the drilling fluid is an aqueous drilling fluid;

conducting a reactivity test for the aqueous drilling fluid; and determining that a reactivity test result, a trend of reactivity test results, or both are outside of a design specification, wherein the drilling fluid adjustment is further based on the determining that the reactivity test result, the trend of reactivity test results, or both are outside of a design specification.

11. The computing system of claim 10, wherein:

the operations further comprise in response to the determining that the reactivity test is outside of the design specification, determining that the drilling fluid inhibition factor is out of specification; and the drilling fluid adjustment comprises returning the drilling fluid inhibition factor to within the specification.

12. The computing system of claim 11, wherein the operations further comprise:

in response to the determining that the reactivity test is outside of the design specification, determining that the drilling fluid inhibition is not out of specification; and in response to the determining that the drilling fluid inhibition is not out of specification:

determining that bit balling is occurring in the drill bit; and automatically initiating one or more bit balling remediation processes.

13. The computing system of claim 11, further comprising adjusting a drilling fluid inhibition specification based at least in part on a combination of the drilling efficiency and the drilling fluid inhibition factor.

14. The computing system of claim 8, wherein the operations further comprise:

determining that the drilling fluid is a non-aqueous drilling fluid; and determining that there is not water in a filtrate collected during a high pressure high temperature test, wherein the drilling fluid adjustment comprises an adjustment to a fluid loss control agent concentration in response to the determining that there is not water in the filtrate.

15. A system, comprising:

a drilling rig including a drill string extending therefrom into a well, the drill string including a drill bit deployed into the well, the drilling rig circulating a drilling fluid in the well;

an electronic drilling recording system coupled to the drilling rig and configured to measure one or more parameters thereof, a drilling efficiency being directly measured or calculated based on the measured one or more parameters;

one or more sensors configured to measure one or more properties of the drilling fluid circulating in the well; and one or more processors configured to perform operations, the operations comprising:

determining that the drilling efficiency is lower than expected;

determining whether a property of a subterranean formation in which the drill bit is positioned has changed based on one or more measurements of the one or more sensors; and in response to determining that the drilling efficiency is lower than expected and the determining that the subterranean formation has changed:

determining that the drilling fluid is a non-aqueous drilling fluid;

calculating a stability of the non-aqueous drilling fluid;

determining that the stability is not acceptable;

conducting a secondary emulsifier pilot test to determine a secondary emulsifier, determining an additive history representing a timeline of fluid additives added to the drilling fluid; and the drilling rig automatically performing a drilling fluid adjustment to the drilling fluid being circulated by the drilling rig, the drilling fluid adjustment being based at least in part on one or more of a drilling fluid inhibition factor or a drilling fluid stability factor, wherein the drilling fluid adjustment includes one or more emulsifier concentration changes to attempt to increase the stability of the non-aqueous drilling fluid, and wherein the drilling fluid adjustment is further based at least in part on the additive history.

16. The system of claim 15, wherein the operations further comprise:

determining that the drilling fluid is an aqueous drilling fluid;

conducting a reactivity test for the aqueous drilling fluid; and determining that a reactivity test result, a trend of reactivity test results, or both are outside of a design specification, wherein the drilling fluid adjustment is further based on the determining that the reactivity test result, the trend of reactivity test results, or both are outside of a design specification.

17. The system of claim 16, wherein:

the operations further comprise, in response to the determining that the reactivity test is outside of the design specification, determining whether the drilling fluid inhibition factor is out of specification;

in response to determining that the drilling fluid inhibition factor is out of specification, the drilling fluid adjustment comprises returning the drilling fluid inhibition factor to within the specification; and in response to the determining that the drilling fluid inhibition is not out of specification:

determining that bit balling is occurring in the drill bit; and automatically initiating one or more bit balling remediation processes.

18. The system of claim 17, further comprising, in response to the determining that the drilling fluid inhibition factor is out of specification, adjusting a drilling fluid inhibition specification based at least in part on a combination of the drilling efficiency and the drilling fluid inhibition factor.

19. The system of claim 15, wherein the operations further comprise:

determining that there is not water in a filtrate collected during a high pressure high temperature test, wherein the drilling fluid adjustment comprises an adjustment to a fluid loss control agent concentration in response to the determining that there is not water in the filtrate.

* * * * *